United States Patent [19]

Roos et al.

[11] Patent Number: 4,775,833
[45] Date of Patent: Oct. 4, 1988

[54] LODGED DEBRIS DETECTOR FOR A PARTICLE ANALYZER

[75] Inventors: Ermi Roos, Miami Lakes; Wallace H. Coulter, Miami Springs, both of Fla.

[73] Assignee: Coulter Electronics, Inc., Hialeah, Fla.

[21] Appl. No.: 915,185

[22] Filed: Oct. 3, 1986

[51] Int. Cl.$^4$ .......................................... G01N 27/00
[52] U.S. Cl. .................................. 324/71.1; 324/71.4; 377/12
[58] Field of Search ............. 324/438, 439, 450, 71.1, 324/71.4; 361/110, 89, 94; 377/12, 30

[56] References Cited

U.S. PATENT DOCUMENTS

| | | | |
|---|---|---|---|
| 3,259,891 | 7/1966 | Coulter et al. | 377/12 X |
| 3,938,038 | 2/1976 | Campbell | 377/12 X |
| 3,978,374 | 8/1976 | Rohr | 361/110 |
| 3,987,391 | 10/1976 | Hogg | 377/12 X |
| 4,326,230 | 4/1982 | Becker et al. | 361/89 X |
| 4,412,175 | 10/1983 | Maynarez | 324/71.1 |
| 4,558,310 | 10/1985 | McAllise | 361/94 X |
| 4,590,533 | 4/1986 | Murata | 361/89 X |
| 4,680,552 | 7/1987 | Shirato et al. | 324/450 X |

*Primary Examiner*—M. H. Paschall
*Assistant Examiner*—A. Jonathan Wysocki
*Attorney, Agent, or Firm*—Harry W. Barron; Gerald R. Hibnick

[57] ABSTRACT

A debris detector for a particle counter, such as a blood cell counter, of the COULTER (R) type. When a particle, or transient debris, passes through the sensing orifice of the particle detector, a voltage pulse occurs; whereas, when debris lodges in or against the orifice of the particle detector, a d.c. voltage shift occurs. The voltage at the orifice is capacitively coupled to an amplifier and the output of the amplifier is integrated. The capacitor coupling the orifice voltage to the amplifier causes an undershoot voltage at the trailing edge of each particle or transient debris pulse, such that a zero average voltage is applied to and, hence, from the amplifier for each voltage pulse. The integrated voltage is applied to a voltage comparator to provide an output signal therefrom whenever the integrated voltage exceeds a reference voltage. The comparator output signal is provided to a delay circuit having a delay related to the time required for a particle to pass through the COULTER detector orifice. If the comparator signal remains after the delay time, a debris alarm signal is provided. This occurs only if a d.c. voltage shift had occurred, since there is no trailing edge, and hence no undershoot to return the integrated voltage to zero prior to the delay time.

21 Claims, 3 Drawing Sheets

LODGED DEBRIS DETECTOR FOR A PARTICLE ANALYZER

BACKGROUND OF THE INVENTION

This invention relates to a debris detector and more particularly to such a detector for use in a particle counter such as a blood cell counter, for detecting and providing an alarm signal whenever debris becomes lodges against or in the orifice through which the particles pass.

Blood cell counters of the general type now known as the COULTER COUNTER (R) analyzer were first described in the U.S. Pat. No. 2,656,508 which was granted Oct. 20, 1953 in the name of Wallace H. Coulter. According to the principle taught by Coulter in the aforementioned patent, a fluid containing blood cells suspended therein, such as diluted whole blood, is passed through a small opening, or orifice, from one fluid containing chamber to another fluid containing chamber. An electrode positioned in each of the chambers is coupled to a current source, so that a constant current flows through the orifice from one chamber to the other. As blood cells pass through the orifice, the electrical resistance within the orifice increases with a corresponding increase in the voltage across the orifice due to the constant current. Sensing means coupled to the two electrons sense the voltage pulse increase due to the package of a particle through the orifice, thereby detecting such particle. By utilizing appropriate counter means and volume control means, the number of particles, such as red blood cells, within a defined volume, can be determined. The change in resistance in the orifice due to the presence of a particle is approximately proportional to the volume of the particle. Thus, the COULTER COUNTER analyzer is capable of determining the mean particle volume of, as well as the number of particles in, a sample being measured.

One of the problems which always has been present in any blood cell counter of the type described above is that debris, such as blood clots or other contaminants placed in the specimen under test from the ambient, can lodge against or within the orifice, thereby preventing the free and natural flow of the cells through the orifice. Other debris within the specimen may be so small that it passes through the orifice, causing no permanent problem. Such small debris is referred to herein as transient debris and sufficient care can be taken so that the number of transient debris particles passing through the orifice is negligible compared to desired particles. Thus, the transient debris, if counted as particles, causes negligible effect on the final result.

Many attempts have been made in the past to provide a detector to indicate that the orifice of the COULTER (R) type particle counter has become clogged by debris lodged in or against the orifice. For example, in U.S. Pat. No. 3,259,842 in the name of Wallace H. Coulter et. al., a debrils detector is described which measures the height and width of the pulses detected by the COULTER particle detector apparatus. This debris detector makes use of the fact that debris generally has a resistance greater than the resistance of a normal blood cell. Further, the duration of the pulse detected for a debris particle or lodged debris generally exceeds the duration of a normal cell. This is because a cell passes through the orifice in less time than debris, because the cell is smaller.

A second type debris detector is disclosed in U.S. Pat. No. 3,259,891, in the name of Wallace H. Coulter et. al., and utilizes similar larger resistance and pulse width for debris versus predictably known lower resistance and pulse time for normal particles passing through the orifice. In the debris alarm detector of U.S. Pat. No. 3,259,891 the magnitude of the voltage sensed is first detected and, for pulses exceeding a certain threshold voltage amplitude, the duration of the pulse is also measured. If the duration exceeds a certain value, then the debris alarm is sounded. The problem with this type of detection is that transient debris and many large particles are detected as debris, merely because of their large size and long duration their pulse.

Several problems exist with the technique in the debris alarm described in U.S. Pat. No. 3,259,891. First, the debris alarm of the prior art is unable to differentiate easily between debris which lodges in or against the orifice and large cells or transient debris which passes through the orifice causing negligible effect on the ultimate result. Further, in the prior art device the waveform shape becomes critical in detecting the debris. This is particularly true of the rise time of the pulse which results when debris becomes lodged in or against the orifice. In order to compensate for the relatively slow rise time of the leading edge of the debris pulse, the prior art device used a lower threshold voltage setting than was optimally desirable. This, in turn, resulted in many false alarms of debris being detected, particularly when the debris was transient debris which passed through the orifice. Further, the prior art device had difficulty in differentiating in many instances between large pulses due to large cells or debris, again leading to many false negatives alarms.

Attempts to overcome many of the limitations of the prior art debris detectors described in the aforementioned patent have been made. For example, in U.S. Pat. No. 4,412,175 in the name of Franklin D. Maynarez, bad pulses are detected based on the techniques of the aforementioned prior art patents to W. H. Coulter, et. al. and ratioing techniques are utilized to determine when the number of bad pulses exceeds certain predetermined unacceptable levels. By utilizing the improvements such as in the Maynarez patent, some of the shortcomings of the prior art detectors can be overcome. Another example of improvements in debris alarms of the prior art is shown in U.S. Pat. No. 4,450,435 in the name of Bobby D. James. In the James Patent, sophisticated comparator means are utilized for comparing the number of good pulses and bad pulses and for alarming when the number of bad pulses exceeds certain predetermined relative per cents. Even with these techniques, false negatives are obtained when the sample under test contains many large cells.

Rather than relying on ratioing and group comparison techniques of the prior art, it would be preferable to be able to utilize the debris alarm circuitry itself directly to provide an indication when debris becomes lodged in the particle counter orifice. This will result in an alarm when troublesome debris is detected, rather than requiring a wait until after the proper ratios or comparisons have been made. Such a wait causes a substantial number of improper particles having been counted. Further, by detecting the debris when it initially becomes lodged, samples may be saved and evasive action taken immediately.

SUMMARY OF THE INVENTION

In accordance with one aspect of this invention, there is provided a debris detector for a particle analyzer of the type having a small orifice separating two chambers, with a constant current applied through the orifice, and in which particles and debris, suspended in a liquid, are passed through the small orifice, whereby each particle or debris passing through the orifice causes a voltage pulse across the orifice and debris lodging in or against the orifice causes a d.c. voltage shift across the orifice. Further, the detector has sensing means to sense the voltage across the orifice. The improvement of the debris detector comprises capacitance means coupling the sensing means to the orifice and means for integrating the output of the sensing means. The improved detector also has means for determining if the integrated sensing means output exceeds a certain value after a certain delay time.

BRIEF DESCRIPTION OF THE DRAWINGS

One preferred embodiment of the subject invention is hereafter described with specific reference being made to the following figures in which.

DETAILED DESCRIPTION

Figure 1:
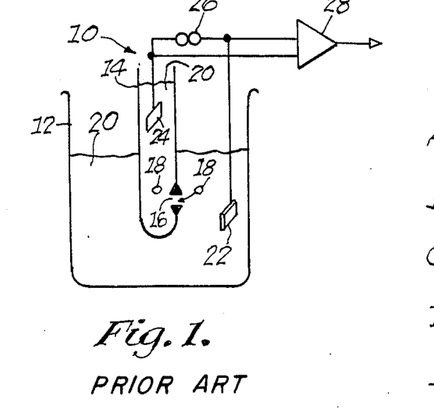
FIG. 1 shows a general schematic representation of the prior art COULTER type particle sensing apparatus.

Referring now to FIG. 1, the traditional schematic presentation of a COULTER type particle sensing apparatus 10, typical of the prior art, is shown. The apparatus 10 includes a first fluid holding container 12 and a second fluid holding container 14. A small aperture, orifice or opening 16 is fabricated in container 14 to allow particles 18, suspended in a fluid 20, to pass from the container 12 into the container 14. A pair of electrodes 22 and 24 are respectably positioned within the fluid 20 of each of containers 12 and 14; and a current source 26 is coupled between the electrodes 22 and 24, so that a constant current flows from electrode 22 to electrode 24 through orifice 16. In addition, sensing, sizing and counting circuit 28, well known in the prior art, is connected to each of electrodes 22 and 24 to provide the detection, size and count of the number of particles 18 passing through orifice 16. This count is generally taken during the controlled provision of a predetermined amount of fluid 20 through orifice 16.

The apparatus of FIG. 1 works extremely well, except when a particle of debris becomes lodged in or against orifice 16. This either causes the particles 18 to cease or slow down in passing through orifice 16, at least for the period of time that the debris is lodged in or against orifice 16, or it causes particles to be improperly sized because of constriction in the orifice volume. It is important to be able to detect this occurrence of debris lodging in or against orifice 16 in order to stop the count and provide an alarm notifying the operator of apparatus 10 that the count or particle volume then occurring is an error and that corrective action must be taken. However, care must be taken to be sure that the debris detected is lodged debris, rather than large cells or transient debris which passes through orifice 16 and thereby does not prevent a significant number of particles 18 from passing through orifice 16. The only harm which results from a piece of transient debris passing through orifice 16 is that the particle count may be increased by one, and/or that the mean particle volume is changed slightly. However, the amount of error from other portions of apparatus 10 is greater than the error which will result in the total count or mean particle volume if transient debris is sensed as if particles. This, of course, assumes that normal care is used in preparing the solution placed in container 12, which contains the particles 18 to be detected, so that debris is minimized.

Figure 2:
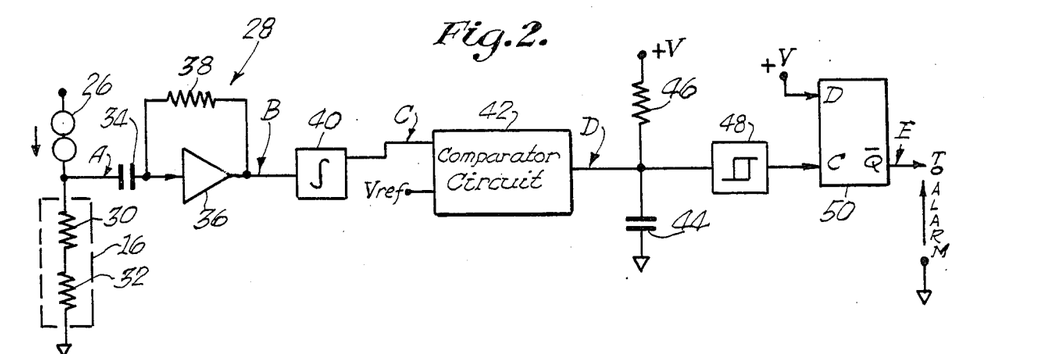
FIG. 2 shows a block diagram of the subject invention used to detect debris lodged in or against the orifice of the apparatus shown in FIG. 1.

Referring now to FIG. 2, orifice 16 is shown schematically as a pair of series coupled resistors 30 and 32. Resistor 30 is the normal resistance in orifice 16 due to the electrolyte fluid 20 normally within aperature 16. Resistor 32 represents a transient resistance which comes and goes as a particle 18 passes through aperature 16. With current source 26 coupled in series with resistors 30 and 32, the voltage across resistors 30 and 32 increases due to the presence of a particle 18 being within aperature 16 which causes a corresponding increase in resistance of resistor 32.

The junction between current source 26 and resistor 30 is coupled through a coupling capacitor 34 to the input of an operational amplifier 36. Amplifier 36, together with feedback resistor 38 and other resistors (not shown) normally associated with an operational amplifier to cause significant gain, represent the first stage of the preamplifier of the sensing portion of circuit 28 shown in FIG. 1. It should be understood that the additional stages of the preamplifier, as well as the post amplifier, generally are included as part of circuit 28, but are not shown in FIG. 2 because they form no part of the subject invention.

The output from amplifier 36, the first stage preamplifier, is applied as an input to an integrator circuit 40. Integrator circuit 40 provides a voltage at its output which is the mathematical integral of the voltage applied to its input. Integrator circuit 40 can include an operational amplifier with a feedback capacitor and is shown in more detail hereafter in FIG. 5. The output from integrator circuit 40 is provided as the data input to a comparator circuit 42. A reference voltage, Vref, also is provided to a second input of comparator circuit 42. The output from comparator circuit 42 is normally a positive voltage whenever the voltage provided at the data input from integrator 40 exceeds the value of the reference voltage Vref. However, the output of comparator 42 is coupled between the junction of one end of each of a capacitor 44 and a resistor 46; the other end of resistor 46 is coupled to a source of positive voltage +V and the other end of capacitor 44 is coupled to ground. When the output of comparator circuit 42 is low, due to the data signal from integrator 40 being less than Vref, the output transistor (not shown) included within comparator 42 is conductive to ground and capacitor 44 discharges therethrough. However, when the voltage provided from integrator 40 to comparator 42 exceeds Vref, capacitor 44 begins charging, with a time constant determined by the values of resistor 46 and capacitor 44.

The junction of resistor 46 and capacitor 44 is coupled as one input to a threshold circuit 48, such as a Schmidt trigger circuit. When the value of the voltage stored by capacitor 44 exceeds threshold value of threshold circuit 48, which may be 1.6 volts for example, the output of circuit 48 changes states. The output from threshold circuit 48 is provided to the clock input (C) of a flip-flop circuit 50 and the leading edge of the threshold circuit 48 pulse forces the Q bar output of flip-flop 50 to a low value, that is, to the logic value opposite to the logic value of the signal applied to its data input (D). This results in a positive to negative voltage appearing at the Q bar output of flip-flop 50. This signal is used to trigger a debris detected visual and/or audible alarm (not shown), thereby alerting the operator to take appropriate action.

Figure 3:
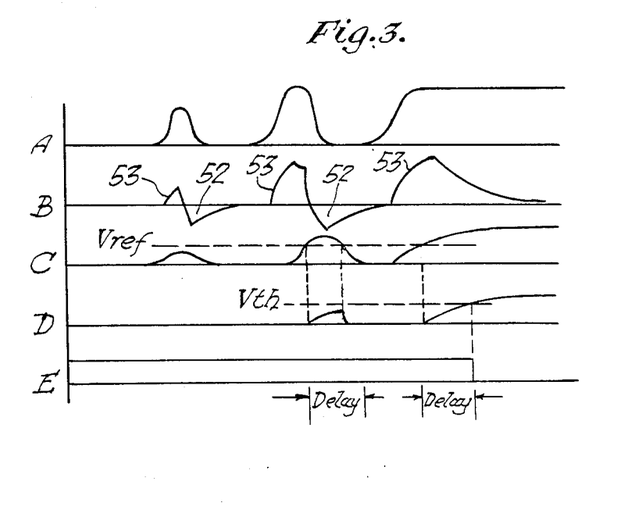
FIG. 3 shows diagrams useful in understanding the general operation of the invention subject matter shown in FIG. 2.

Referring now to FIG. 3, a series of waveforms labeled A–E are shown. Corresponding letters A–E are shown in FIG. 2 to indicate which portion of the circuit the waveforms A–E represent. Waveform A is the voltage pulses provided by detecting the change in voltage due to the presence or absence of transient resistor 32 due to the corresponding presence or absence of a particle 18 passing through orifice 16. As can be seen, the first voltage pulse is a relatively low signal and manifests a normal blood cell passing through orifice 16. The second pulse in waveform A represents either a larger blood cell, or transient debris, either of which have a higher resistance that results in a higher voltage. However, because the large cell or transient debris passes through orifice 16, the pulse has only a slightly longer than normal pulse width. The third portion of waveform A represents a piece of debris which has become lodged in or against, and thereby blocks, orifice 16. This results in a high voltage being sensed for a long duration. In effect, the result is a d.c. voltage shift for the voltage sensed.

Waveform B of FIG. 3 shows the output of operational amplifier 36, which as previously mentioned, is the first stage of the preamplifier of circuit 28 shown in FIG. 1. Waveform B shows the effects of capacitor 34 being included between aperature 16 and the first stage of the preamplifier. As can be seen, the first pulse in Waveform B increases at a slower rate than the corresponding A waveform pulse, because capacitor 34 becomes charged and subtracts its voltage from the A waveform pulse. It is well known that the voltage across a capacitor cannot instantaneously change. Thus, when the trailing edge of the first pulse occurs, a negative undershoot 52 in the voltage provided from the output of amplifier 36 results. The amplitude of this negative undershoot is approximately equal to the amount the rising edge of the pulse has been depressed by the charging of capacitor 34. The second pulse in waveform B is substantially identical to the shape of the first pulse of waveform B, except that its magnitude is larger, due to the larger pulse being detected. However, again, an undershoot 52 is present in the second pulse in waveform B.

For any value of capacitor 34, the area above undershoot 52 is equal to the area below the positive going portion 53 of the first and second pulses in Waveform B. Thus, the average voltage passing through amplifier 36 is zero for the first and second pulses in Waveform B.

It should be recalled from the description of waveform A that the third pulse rises to a steady d.c. voltage and remains at that d.c. voltage value due to the debris becoming lodged in or against orifice 16. The third pulse of waveform B reflects this constant voltage by the absence of any undershoot 52. The value of the output of operational amplifier 36 for the third pulse thus rises to a peak value and therafter decays from the peak value to zero. Thus, the average value of the voltage through amplifier 36 for the third pulse is no longer zero.

Referring now to waveform C of FIG. 3, the first and second pulses are similarly shaped and different only in amplitude. Both rise and fall back to zero due to the integration of the positive portion 53 and undershoot portion 52 of the first and second pulses of waveform B. However the third pulse of waveform C increases to a value at which it generally remains. Again, this is because the integration of the third pulse in waveform B does not include any undershoot to bring the integral thereof back to zero.

Waveform C, as indicated in FIG. 2, is applied to the input of comparator circuit 42, which also has the voltage Vref applied thereto. Voltage Vref is shown as a dashed line in waveform C and is above the first pulse and through the second pulse and third pulse of waveform C.

Referring now to waveform D of FIG. 3, it is seen that since the first pulse of waveform C was below the Vref threshold, there is no corresponding first pulse in waveform D. The pulse of waveform D corresponding to the second pulse of waveform C, however, exists for the period of time that the second pulse of waveform C was above the threshold Vref value. However, this is a relatively short time due to the short duration of the second pulse detected at Waveform A. Since the waveform D pulses represent the voltage stored by capacitor 44, the waveform D pulses only begin increasing when the waveform C pulses exceed the comparator Vref voltage and capacitor C is being charged. Thereafter, capacitor C discharges through the grounded output of comparator circuit 42. Thus, there is no pulse in waveform D corresponding to the first pulse in waveform C and the pulse of waveform D corresponding to the second pulse of waveform C never exceeds the threshold voltage Vth. The third pulse of waveform C, however, remains above the Vref value, so capacitor 44 continues to be charged until it exceeds the threshold voltage Vth of threshold circuit 48. This is shown by the dashed lines labeled Vth in waveform D.

Referring now to waveform E of FIG. 3, as soon as the last pulse of waveform D exceeds the Vth value, an output appears from circuit 48, triggering flip-flop 50 and causing the voltage E to change state. This will be interpreted by circuitry (not shown) to cause an audible and/or visual alarm to occur, manifesting to the operator of apparatus 10 that a debris blockage has been detected.

Figure 4:
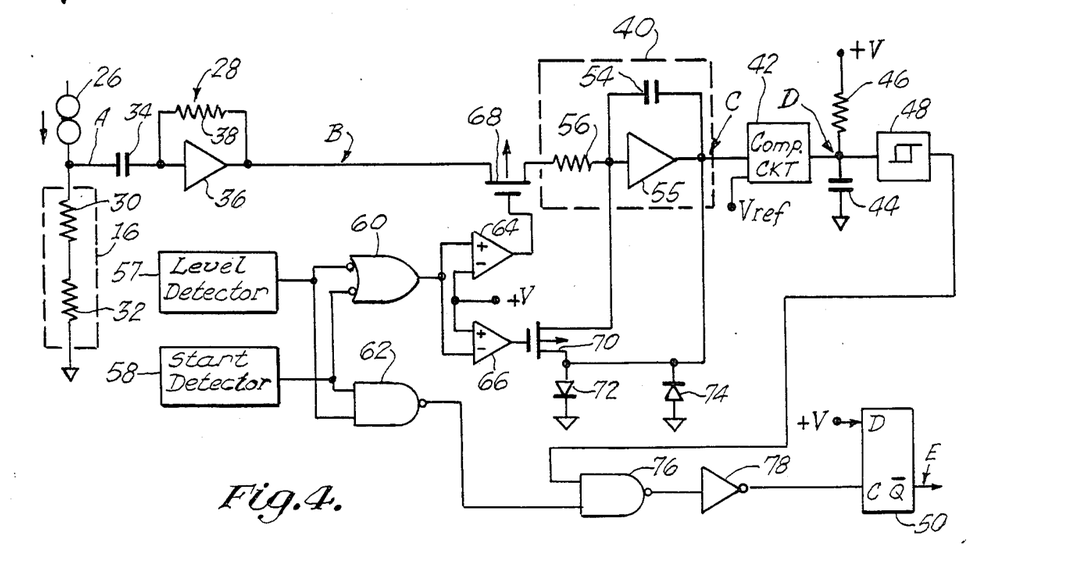
FIG. 4 shows logic circuitry which has been added to the block diagram shown in FIG. 2 to inhibit its operability during certain special periods.

Referring now to FIG. 4, an enhanced embodiment of the subject invention is shown. The circuit in FIG. 4 includes means to inhibit the operation during the critical times of the start-up of apparatus 10, or the detection of the filling of a chamber containing fluid 20. This chamber (not shown) can be one used for determining hemoglobin in a blood sample. Hemoglobin is measured by techniques independent of the COULTER principle. When the chamber used for measuring hemoglobin has filled, the fluid 20, mixed with a chemically treated blood sample, strikes an electrode that is positioned at the location the liquid would reach when the chamber is filled. A second electrode is at the bottom of the chamber. When the liquid touches the level sensing electrode, circuitry (not shown) detects the liquid level by sensing electrical continuity between the sensing electrode and the bottom electrode. This continuity detection is accomplished by current flow between the electrodes. This current flow causes interference at the orifice 16 that is similar to debris being lodged against or in the orifice. Both the start up and filling of the chamber can cause transient voltages to be provided at the input side of capacitor 34, and hence to amplifier 36, which may appear as permanent blockages due to debris, but in fact are due to nonpermanent transient voltages resulting from either the application of power to apparatus 10 or the flow of electrical current resulting from detection of the filling of a chamber containing fluid 20.

In FIG. 4, like components, with respect to Figure 2, have been given like numeral designations and the operation thereof is similar to that described with respect to FIG. 2. Of the components shown in FIG. 2, only integrator 40 is shown in more detail as including a feedback capacitor 54, an operational amplifier 55 and an input resistor 56. This, as is well known in the art, is a conventional integrator circuit.

The additional circuitry added in FIG. 4 includes a level detector 57 and a start detector 58. Both are well known in the art and are shown only in block form in Figure 4. Level detector 57 provides a voltage whenever the level of the fluid 20 in the hemoglobin chamber reaches a prescribed level. When the fluid reaches the prescribed level in that chamber (not shown), the level is detected by current flow caused by continuity produced when the fluid reaches the level sensing electrode. This current could be detected as a d.c. level shift not always indistinguishable from a similar d.c. level shift as a result of blocking debris. Start detector 58, on the other hand, monitors when voltage is first applied to apparatus 10. Such application results in a significant d.c. voltage shift through orifice 16, which again could be detected as lodged debris causing a d.c. voltage shift in orifice 16. The output voltage from level detector 57 is a pulse of approximately 100 milliseconds duration and the output voltage of start detector 58 is a pulse of approximately one second duration which, as will be explained hereafter, inhibits the operation of the detector circuit.

The output of level detector 57 and the output of start detector 58 are both applied as the two inputs to a NAND gate 60. In addition, the outputs of level detector 57 and start detector 58 are applied as the two inputs to a NAND gate 62. The output from NAND gate 60 is provided to the noninverting input of a driver circuit 64 and the inverting input of a driver circuit 66. The inverting input of driver circuit 64 and the noninverting input of driver circuit 66 are coupled to a source of positive voltage +V. The output of driver circuit 64 is coupled to the gate of a field effect transistor (FET) transistor 68. The channel electrodes of transistor 68 are coupled between operational amplifier 36 and the input to operational amplifier 55 within integrator circuit 40 through the input resistor 56.

The output of driver circuit 66 is coupled to the gate electrode of an FET transistor 70, which has one channel electrode coupled to the junction between resistor 56 and the input to operational amplifier 55 and the other channel electrode coupled to the anode of a diode 72, the cathode of which is coupled to ground. In addition, the other channel electrode of FET transistor 70 is coupled to the output of operational amplifier 55 and to the cathode of a diode 74, the anode of which is coupled to ground.

Capacitor 54 is coupled between the input and output of operational amplifier 55, and thus, is coupled in the same manner as the channel electrodes of transistor 70. Whenever either level detector 57 or start detector 58 detects a respective level change or voltage application, a signal is provided through NAND gate 60 and driver circuit 64 to render FET transistor 68 nonconductive and FET transistor 70 conductive. This occurs for the approximately 100 millisecond period following level detector 57, or the one second period following start detector 58 detecting one of the critical conditions. During this period, capacitor 54 is discharged through now conductive FET transistor 70. At the same time, voltage is prevented from being applied to the input of integrator 40 by nonconductive FET transistor 68. After the 100 millisecond or one second duration of the pulses provided by one of detectors 57 and 58, the normal condition of transistor 68 being conductive and transistor 70 being nonconductive is returned and operation proceeds as previously explained.

In addition, the outputs from detectors 57 and 58 are applied through NAND gate 62 to disable a NAND gate 76 from passing any signals provided thereto from threshold circuit 48. Because of the inclusion of NAND gate 76, it is necessary to provide an inverter 78, in order to have the proper polarity to trigger flip-flop 50 by providing a pulse to the clock (C) input thereof.

Figure 5:
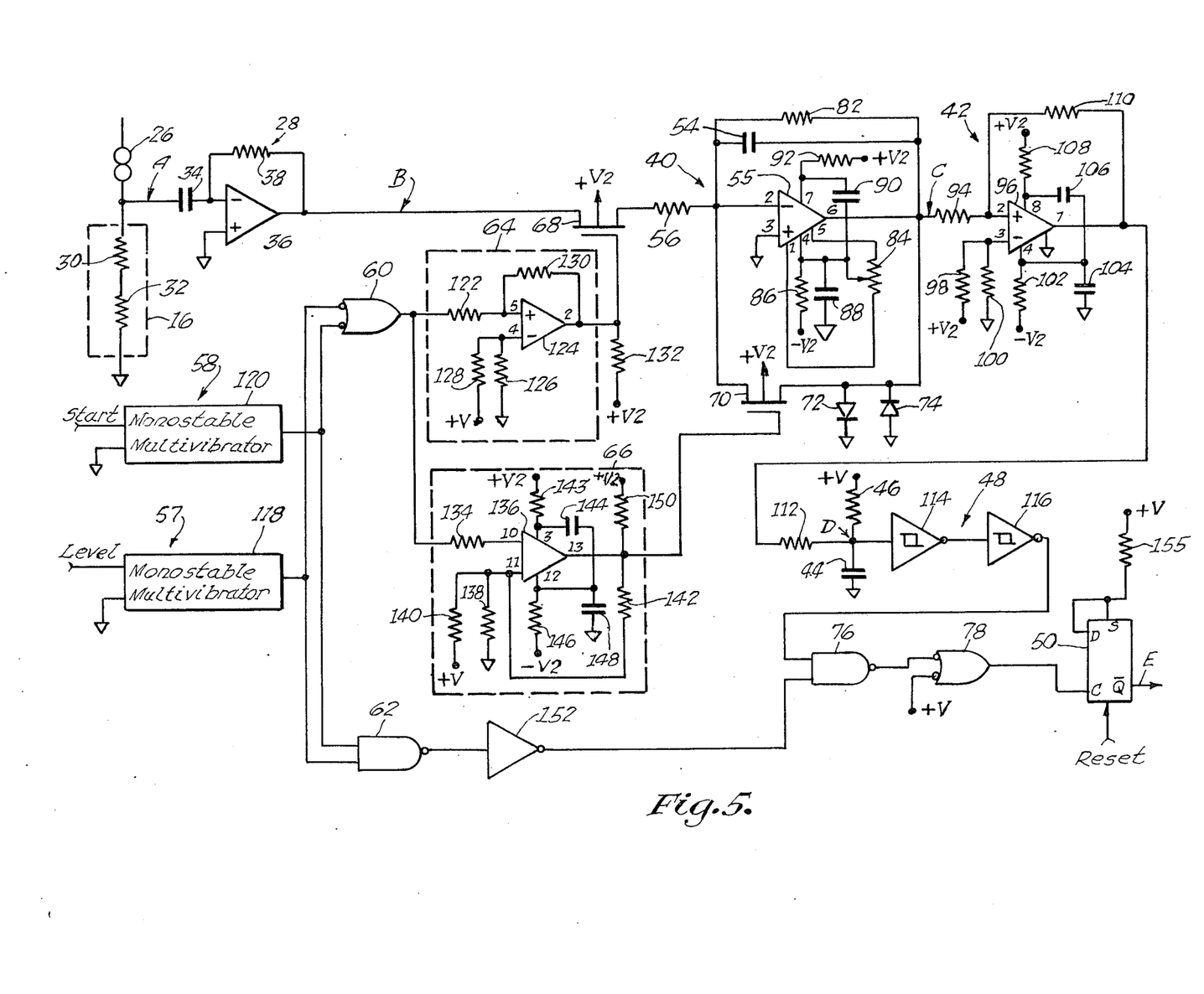
FIG. 5 shows a more detailed circuit diagram of the block diagram shown in FIG. 4.

Referring now to FIG. 5, a more detailed schematic diagram of the circuit shown in FIG. 4 is shown. Where like components are shown, they have been given like numerical designations with respect to the circuits shown in FIGS. 4 and 5. Elements 26 through 38 (even numbers only) and FET transistor 68 are connected as previously described with respect to FIG. 4. The substrate electrode of transistor 68 is coupled to a source of voltage +V2, which can be 15 volts d.c. The previously mentioned voltage +V can be five volts d.c. The other channel electrode of transistor 68 is coupled through resistor 56 to the inverting input of operational amplifier 55. One channel electrode of transistor 70 is connected to the inverting input of operational amplifier 55 and the other channel electrode of transistor 70 is connected to the output of operational amplifier 55. The substrate electrode of transistor 70 is connected to a source of voltage +V2. Capacitor 54 is coupled between the output and the inverting input of operational amplifier 55. A resistor 82 is coupled in parallel with capacitor 54 and serves to discharge capacitor 54 after a debris alarm has sounded and to prevent the debris alarm from responding to very slowly varying d.c. level shifts at the orifice 16, which are not caused by debris. The anode of diode 72 is connected to the output of operational amplifier 55 and the cathode of diode 72 is connected to ground. The cathode of diode 74 is connected to the output of operational amplifier 55 and the anode of diode 74 is connected to ground. Connected in this manner, diodes 72 and 74 limit the voltage excursion of the output of operational amplifier 55.

The noninverting input of amplifier 55 is coupled to ground. The numbers at the connections of some of the components shown in FIG. 5 are pin numbers of the particular components used. A list of the components used is given hereafter. Offset voltage control input, pin 1, of amplifier 55 is coupled through a potentiometer 84 to offset voltage control input, pin 5, of amplifier 55. Potentiometer 84 is used to set the offset voltage of operational amplifier 55. Negative d.c. power supply input, pin 4, of amplifier 55 is coupled through a resistor 86 to −V2 volts, which can be −15 volts, through a capacitor 88 to ground and through a capacitor 90 to positive d.c. power supply input, pin 7. The junction between capacitor 90 and positive d.c. power supply input, pin 7, is coupled through a resistor 92 to voltage V2. Resistors 86 and 92 and capacitors 88 and 90 provide for d.c. power supply bypassing of amplifier 55.

The output from amplifier 55 is coupled through a resistor 94 to the noninverting input of a comparator 96, which forms the principal component of the comparator circuit 42 shown in FIGS. 2 and 4. The reference voltage is applied to the inverting input of comparator 96 and is provided by the inverting input being coupled through a resistor 98 to voltage V2 and through a resistor 100 to ground. Negative d.c. power supply input, pin 4, of comparator 96 is coupled through a resistor 102 to voltage -V2 and through a capacitor 104 to ground. The junction between negative d.c. power supply input, pin 4, and capacitor 104 is also coupled through a capacitor 106 to positive d.c. power supply input, pin 8. Positive d.c. power supply input, pin 8, also is coupled through a resistor 108 to +V2 voltage. Resistors 102 and 108, and capacitors 104 and 106 provide for d.c. power supply bypassing for comparator 96. The output from comparator 96 is coupled through a resistor 110 back to the input thereof. Resistor 110 provides hysteresis for comparator 96, thus stabilizing its operation when the noninverting voltage is near the reference voltage. Connected in this manner, comparator circuit 42 provides a positive voltage at its output whenever the voltage at the non-inverting input exceeds the threshold voltage, for example, 0.36 volts. Thus, whenever the output from integrator 40 applied through resistor 94 is above 0.36 volts, the output of comparator 96 becomes a positive voltage.

The voltage from the output of comparator 96 is provided through a resistor 112 to the junction between resistor 46 and capacitor 44. As previously mentioned, this junction also is coupled to threshold circuit 48, which consists of two Schmidt trigger circuits 114 and 116, both of which invert the signal applied thereto.

Level detector 57 includes means (not shown) for detecting if a chamber containing fluid 20 has filled, for providing a trigger signal (LEVEL) to a monostable multivibrator 118. Similarly, means to detect the application of power to aperatus 10 causes a trigger signal (START) to be provided to a monostable multivibrator 120. Both multivibrators 118 and 120 have associated time constant setting components (not shown) which cause either a 100 millisecond or a one second low voltage pulse to be provided at the outputs thereof upon application to either one of the LEVEL or START signals.

The output of NAND gate 60 is coupled through a resistor 122 to the noninverting input of a driver amplifier 124, which is a comparator. The inverting input of amplifier 124 is coupled through a resistor 126 to ground and also through a resistor 128 to voltage +V. Resistors 126 and 128, and voltage +V provide a reference voltage for driver amplifier (or comparator) 124. The output of driver amplifier 124 is coupled through a resistor 130 back to the noninverting input thereof.

Resistor 130 provides hysteresis for driver amplifier 124 in order to stabilize amplifier 124 if its non-inverting input voltage is near its threshold voltage. The output of amplifier 124 also is coupled through a resistor 132 to +V2 and to the gate electrode of transistor 68. Resistor 132 is a pullup resistor for the output of amplifier 124.

The output from NAND gate 60 also is coupled through a resistor 134 to the inverting input of a driver amplifier 136. The noninverting input to amplifier 136 is coupled through a resistor 138 to ground, a resistor 140 to voltage +V and a resistor 142 to the output of amplifier 136. Resistors 138 and 140 (with voltage +V) provide a threshold voltage for amplifier (or comparator) 136, and resistor 142 provides hysteresis for amplifier 136. The positive d.c. power supply input, pin 3, of amplifier 136 is coupled through a resistor 143 to voltage V2 and through a capacitor 144 to negative d.c. power supply input, pin 12. Negative d.c. power supply input, pin 12, also is coupled through a resistor 146 to voltage −V2 and through capacitor 148 to ground. Resistors 143 and 146, and capacitors 144 and 148 are used to provide d.c. power supply bypassing for amplifier 136. In the particular configuration described here, amplifiers 124 and 136 are contained in the same integrated circuit, and therefore use the same power supply inputs. The output of amplifier 136 is coupled through a resistor 150 to voltage +V and to the gate electrode of transistor 70. Resistor 150 is a pullup resistor for the output of amplifier 136.

Further additions to the circuit shown in FIG. 5 include the provision of an inverter 152 between the output of NAND gate 62 and the input of NAND gate 76. Inverter 152 converts NAND gate 62 into an AND gate. In addition, the positive voltage applied to the data (D) input of flip-flop 50 is applied through a resistor 155 and also is applied to the preset input thereof. A RESET signal, which may be provided from an operator controlled switch on the device 10 operator's panel, is provided to the reset input of flip-flop 50.

The following circuit components have been assigned the following values in order to operate in the manner previously described with respect to FIGS. 2 and 4;

| Resistors (ohms) | Capacitors (microfarads) |
|---|---|
| 38–200K | 34–.22 |
| 46–10K | 44–3.3 |
| 80–49.9K (1%) | 54–1.2 |
| 82–1.0 M | 88–.01 |
| 84–100K | 90–.01 |
| 86–47 | 104–.01 |
| 92–47 | 106–.01 |
| 94–2.49K (1%) | 144–.01 |
| 98–10K (1%) | 148–.01 |
| 100–249 (1%) | |
| 102–47 | |
| | Amplifiers and Comparators |
| 108–47 | 55–AD542 |
| 110–249K (1%) | 96–LM311 |
| 112–100 | 124–LM339 |
| 122–4.7K | 136–LM339 |
| 126–1.5K | |
| 128–3.3K | Other Components |
| 130–100K | 50–74LS74 |
| 132–10K | 60–74LS00 |
| 134–4.7K | 62–74LS00 |
| 138–1.5K | 68–3N163 |
| 140–3.3K | 70–3N163 |
| 142–100K | 72–IN4148 |
| 143–47 | 74–IN4148 |
| 146–47 | 76–74LS00 |
| 150–10K | 78–74LS00 |

| -continued | |
|---|---|
| 155—3.3K | 114—74LS14 |
| | 116—74LS14 |
| | 118—74LS221 |
| | 120—74LS221 |
| | 152—74LS14 |

Figure 6:
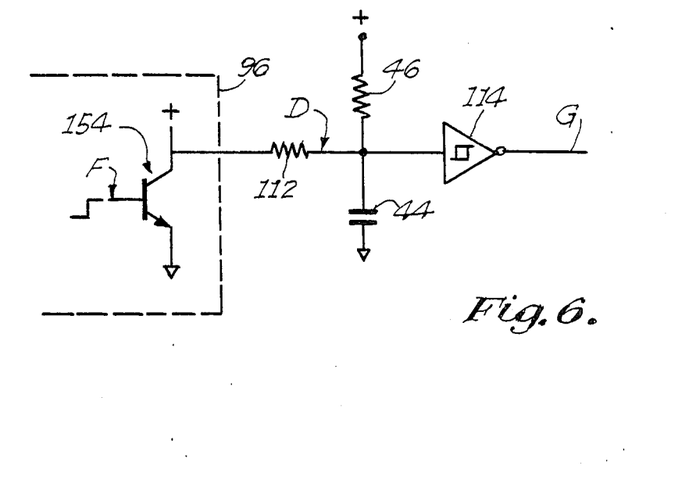
FIG. 6 shows yet a more detailed diagram of a certain portion of the circuit shown in FIG. 5 relating to the operation of the delay function.

Referring now to FIG. 6, the operation of resistor 46 and capacitor 44 in conjunction with the output of amplifier 96 and Schmidt Trigger circuit 114 now will be described. Reference also will be made to the waveforms of FIG. 7 for assistance in understanding the operation of the circuit shown in FIG. 6. Comparator 96 includes an output transistor 154, which is rendered conductive by a positive voltage signal applied to the base thereof when the voltage at the noninverting input is less than the voltage at the inverting input. This allows capacitor 44 to discharge through resistor 112 and conductive transistor 154, so that no voltage is held by capacitor 44. Under this situation, Schmidt Trigger circuit 114 provides a logic high output.

Figure 7:
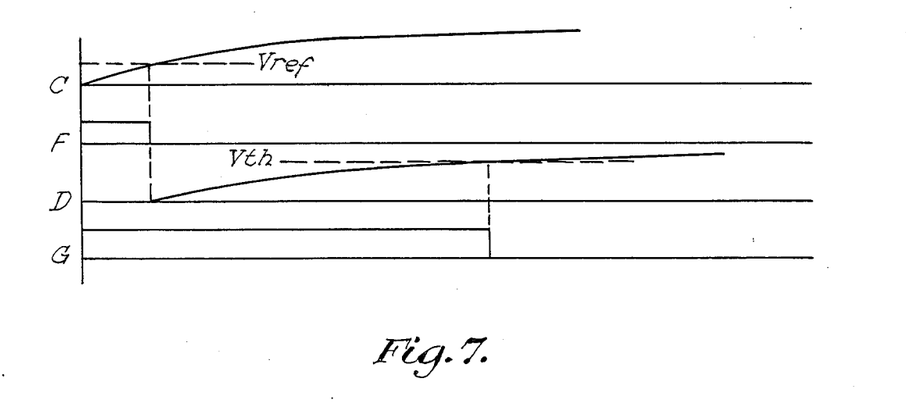
FIG. 7 is a series of waveforms useful in understanding the operation of the circuit shown in FIG. 6.

Once the signal from integrator 40 applied to the nonverting input of amplifier 54 exceeds the reference voltage at the inverting input, as determined by resistors 98 and 100, the signal provided to the base of transistor 154 falls to a low value, thereby rendering transistor 154 nonconductive. This is shown by the waveform F in Figure 7. Waveform C of FIG. 7 is the same signal C indicated earlier in FIG. 3. Once transistor 154 becomes nonconductive by signal F going from a high value to a low value, capacitor 44 begins charging to a value determined by the voltage applied to the other side of resistor 46. This voltage can be 5 volts. The time that is required for capacitor 44 to charge to the full voltage is determined by the time constant of resistor 46 and capacitor 44. These values should be selected together with the voltage applied to the other side of resistor 46 so that the time required for capacitor 44 to charge to 1.6 volts, which is the threshold voltage of Schmidt Trigger 114, will be approximately 3.86 miliseconds. This is sufficient time to allow large particles and transient debris to pass through orifice 16, but a small enough time to detect actual blocking debris within or against orifice 16. Once Schmidt Trigger 114 is triggered by capacitor 44 being charged to 1.6 volts or more, the output thereof, which is waveform G of FIG. 7, becomes a low value, thereby resulting in a debris alarm occurring, as previously explained.

What is claimed is:

1. In a particle detector of the type having a small orifice separating two chambers, with a constant current applied through said orifice, and in which particles and debris suspended in a liquid are passed through said small orifice, whereby each particle or debris passing through said orifice causes a voltage pulse across said orifice and debris lodging in or against said orifice causes a d.c. voltage shift across said orifice, and said detector further having sensing means to sense the voltage across said orifice, the improvement of a debris detector comprising:
capacitance means coupling said sensing means to said orifice;
means for integrating the output of said sensing means; and
means for determining if the integrated sensing means output exceeds a certain value only after a certain delay time.

2. The invention according to claim 1 wherein said capacitance means causes an undershoot of the voltage at the falling edge of each voltage pulse sensed.

3. The invention according to claim 2 wherein said capacitance means maintains a zero average value at the output of said sensing means for voltage pulses detected due to particles and debris passing through said orifice.

4. The invention according to claim 1 wherein said capacitance means maintains a zero average value at the output of said sensing means for voltage pulses detected due to particles and debris passing through said orifice.

5. The invention according to claim 4 wherein said means for determining includes voltage comparator means for providing an output signal in response to the integrated sensing means output being above a certain threshold value said certain delay time after initially being above said certain threshold value.

6. The invention according to claim 4:
wherein said integrating means provides a voltage at its output related to the integral of sensing means output; and
wherein said means for determining includes:
voltage comparator means having one input coupled to said integrating means output and a second input coupled to a source of reference voltage, and an output at which normally appears a voltage pulse having a leading edge whenever the voltage at said integrating means output exceeds said reference voltage;
second capacitance means, including a charge path therefore, coupled to said comparator means output for being charged to above a threshold value during said certain delay time following said voltage at said integrating means output exceeding said reference voltage; and
threshold sensing means for sensing said second capacitance means being charged to a value exceeding said threshold value and for providing a signal manifesting the detection of lodged debris.

7. The invention according to claim 6 wherein said charging path for said second capacitance means includes a resistance and the value of said second capacitance means and said resistance of said charging path are selected to determine said certain delay time.

8. The invention according to claim 7 wherein said second capacitance means discharges whenever said voltage applied to said first input of said comparator means is below said reference voltage.

9. The invention according to claim 6 wherin said second capacitance means discharges whenever said voltage applied to said first input of said comparator means is below said reference voltage.

10. The invention according to claim 9 wherein said detector further includes means for inhibiting said detector for a fixed time following the application of current to said orifice.

11. The invention according to claim 10:
wherein said means for integrating includes a capacitor; and
wherein said means for inhibiting discharges said integrating means capacitor.

12. The invention according to claim 6 wherein said detector further includes means for inhibiting said detector for a fixed time following the application of current to said orifice.

13. The invention according to claim 12:
wherein said means for integrating includes a capacitor; and wherein said means for inhibiting discharges said integrating means capacitor.

14. The invention according to claim 1 wherein said detector further includes means for inhibiting said detector for a fixed time following the application of current to said orifice.

15. The invention according to claim 14:
wherein said means for integrating includes a capacitor; and
wherein said means for inhibiting discharges said integrating means capacitor.

16. A debris detector for a particle counter of the type in which particles suspended in a fluid pass through a small opening, said opening being coupled in circuit with a constant current source, said counter being constructed to allow the voltage across said opening to be sensed, said fluid further containing debris, some of which can at least partially block said opening and other of which passes through said opening, the resistance of said opening increasing during the time a particle or debris pass therethrough and during the time debris is at least partially blocking said opening, the time for a particle to pass through said opening being less than a certain time, said detector comprising:
amplifying means for providing an amplified version of a voltage applied thereto;
means, including a serially connected capacitor, for coupling the voltage sensed across said opening to said amplifying means, said capacitor maintaining a zero average voltage provided to said amplifying means;
integrating means having an input, to which is applied said amplifying means provided voltage, for providing a voltage which is an integrated version of said amplifying means provided voltage; and
threshold means, to which said integrating means signal is applied, for providing a debris alarm signal, manifesting the detection of debris at least partially blocking said opening whenever the amplitude of said integrating means voltage remains above a certain threshold amplitude for at least a time related to said certain time.

17. The invention according to claim 16 wherein said threshold means includes:
voltage comparator means having a first input to which said integrating means signal is provided and a second input to which a constant voltage, having an amplitude related to said threshold amplitude, is applied, said comparator further including an output transistor which changes between the conductive and nonconductive states upon said integrating means voltage amplitude exceeding said constant voltage amplitude; and
a delay circuit, coupled to said output transistor, for providing said debris alarm signal whenever said output transistor remains in the changed state for at least said certain time.

18. The invention according to claim 17 wherein said delay circuit is a resistor and capacitor, in which the capacitor is charged by a voltage applied through the resistor only when said output transistor is in the state associated with said integrating means voltage being above said constant voltage, the values of said resistor, capacitor and voltage charging said capacitor being selected so that said capacitor becomes charged to a threshold voltage related to said threshold amplitude, after said certain time.

19. The invention according to claim 18:
wherein one end of each of said resistor and capacitor are connected together, the other end of said resistor is connected to said voltage and the other end of said capacitor is connected to ground; and
wherein the junction of said resistor and capacitor is connected to the output electrode of said output transistor and as an input to a threshold circuit which provides said debris alarm signal when the voltage across said capacitor is at least as great as the threshold value of said threshold circuit.

20. The invention according to claim 19 further including inhibiting means for inhibiting said integrating means for a defined period after initiation of said device.

21. The invention according to claim 16 further including inhibiting means for inhibiting said integrating means for a defined period after initiation of said device.

* * * * *